US012016531B2

(12) United States Patent
Rentschler et al.

(10) Patent No.: US 12,016,531 B2
(45) Date of Patent: Jun. 25, 2024

(54) ROBOTIC CAPSULE ENDOSCOPE

(71) Applicant: The Regents of the University of Colorado, a body corporate, Denver, CO (US)

(72) Inventors: Mark E. Rentschler, Boulder, CO (US); Gregory Formosa, Boulder, CO (US); Joseph M. Prendergast, Boulder, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 1055 days.

(21) Appl. No.: 16/868,114

(22) Filed: May 6, 2020

(65) Prior Publication Data
US 2020/0352424 A1   Nov. 12, 2020

Related U.S. Application Data

(60) Provisional application No. 62/844,302, filed on May 7, 2019.

(51) Int. Cl.
| A61B 1/04 | (2006.01) |
| A61B 1/00 | (2006.01) |
| A61B 1/06 | (2006.01) |
| A61B 1/31 | (2006.01) |
| A61B 34/00 | (2016.01) |
| A61B 34/20 | (2016.01) |
| A61B 34/32 | (2016.01) |
| A61B 34/30 | (2016.01) |

(52) U.S. Cl.
CPC .......... *A61B 1/041* (2013.01); *A61B 1/00119* (2013.01); *A61B 1/0684* (2013.01); *A61B 1/31* (2013.01); *A61B 34/20* (2016.02); *A61B 34/32* (2016.02); *A61B 34/71* (2016.02); *A61B 2034/2046* (2016.02); *A61B 2034/301* (2016.02)

(58) Field of Classification Search
CPC ......... A61B 1/041; A61B 1/31; A61B 1/0684; A61B 1/00119; A61B 1/00156; A61B 34/72; A61B 2034/303; A61B 34/30
See application file for complete search history.

(56) References Cited

U.S. PATENT DOCUMENTS

| 4,828,276 A * | 5/1989 | Link .................... B23Q 7/043 |
| | | 279/133 |
| 6,824,510 B2 * | 11/2004 | Kim ...................... A61B 34/30 |
| | | 600/101 |

(Continued)

*Primary Examiner* — Anh Tuan T Nguyen
*Assistant Examiner* — Rynae E Boler
(74) *Attorney, Agent, or Firm* — Polsinelli PC

(57) ABSTRACT

A self-propelled semi- or fully-autonomous robotic endoscope device is provided that include multi-degrees of freedom movement and may be sensor-enabled for colonoscopy procedures. The device may include two independently controlled motors configured to drive micro-pillared treads above and below the device, allowing for 2-degrees of freedom (DOF) skid-steering even in a collapsed lumen. The robotic device contains similar functionality of a traditional endoscope, such as a camera, adjustable LEDs, channels for insufflation and irrigation, and a tool port for common endoscopy instruments (e.g., forceps, snares, etc.).

15 Claims, 8 Drawing Sheets

(56) References Cited

U.S. PATENT DOCUMENTS

| | | | | |
|---|---|---|---|---|
| 7,044,245 B2* | 5/2006 | Anhalt | .................. | B62D 57/00 |
| | | | | 180/9.1 |
| 2002/0171385 A1* | 11/2002 | Kim | ....................... | A61B 34/72 |
| | | | | 318/568.12 |
| 2006/0089533 A1* | 4/2006 | Ziegler | .............. | A61B 1/00156 |
| | | | | 600/114 |
| 2010/0318059 A1* | 12/2010 | Farritor | ............. | A61B 1/00188 |
| | | | | 604/82 |
| 2011/0313249 A1* | 12/2011 | Viola | ................ | A61B 1/00101 |
| | | | | 600/114 |
| 2013/0172671 A1* | 7/2013 | Rentschler | ........... | A61B 1/0011 |
| | | | | 156/247 |

* cited by examiner

ROBOTIC CAPSULE ENDOSCOPE

CROSS REFERENCE TO RELATED APPLICATIONS

This application claims priority from U.S. provisional patent application Ser. No. 62/844,302, entitled "Robotic Capsule Endoscope" filed on May 7, 2019, the entirety of which is incorporated by reference herein.

GOVERNMENT SUPPORT

This invention was made with government support under grant numbers 1235532 and 1827787 awarded by the National Science Foundation. The government has certain rights in the invention.

FIELD

Embodiments of the present invention generally relate to medical devices, and more specifically to self-propelled endoscopic devices for use in endoscopy procedures.

BACKGROUND

Endoscopy procedures are the standard method of diagnosing and treating for a variety of lower gastrointestinal (GI) diseases, including colorectal cancers that remain the third most diagnosed and fatal cancers worldwide. Generally, these procedures are performed by manually pushing a long, semi-rigid endoscope through a three-dimensional and tortuous path colon, resulting in a technically challenging procedure. A common issue with colonoscopy procedures in particular is "looping," where the endoscope continues to advance into the colon without a simultaneous progression of the tip, thus distending the colon and causing patient pain. Current attempts to address the challenges associated with GI procedures include active propulsion robotic capsule endoscopes (RCEs). A wide range of locomotion methods for both wireless and tethered RCEs have been attempted including legged, inchworm, treaded, magnetically linked, and even hybrid prototypes, but each category has its own drawbacks. Despite the advances made, commercially available RCEs remain problematic and unreliable for use in colonoscopy procedures.

SUMMARY

An aspect of the present disclosure may include a robotic endoscope device including a housing comprising an upper portion and a lower portion. The robotic endoscope device may also include a first double worm drive shaft, disposed within the housing between the upper portion and the lower portion, comprising a first screw section comprising right-handed spiraling and a second screw section comprising left-handed spiraling, a first worm gear threadably engaged with the right-handed spiraling of the first screw section of the first double worm drive shaft and engaged with a lower continuous track assembly, the first worm gear transmitting rotation of the first double worm drive shaft to rotation of the lower continuous track assembly in a first direction, and a second worm gear threadably engaged with the left-handed spiraling of the second screw section of the first double worm drive shaft, the second worm gear rotating in a second direction opposite the first direction in response to rotation of the first double worm drive shaft. The robotic endoscope device may also include an idler gear threadably engaged with the second worm gear and engaged with an upper continuous track assembly, the idler gear configured to transmit rotation of the second worm gear to rotation of the upper continuous track assembly in a second direction opposite the first direction, Another aspect may include a surgical method for a colonoscopy. The method may include the operations of locating a self-propelled endoscope device in a gastro-intestinal tract of a subject, transmitting a first drive signal to a first motor of the endoscope device to rotate a first double worm drive shaft, wherein rotation of the first double worm drive shaft causes a first upper continuous track assembly to rotate in a first direction and a first lower continuous track assembly to rotate in a second direction opposite the first direction to propel the endoscope device, and transmitting a second drive signal to a second motor of the endoscope device to rotate a second double worm drive shaft independent of the first double worm drive shaft. Rotation of the second double worm drive shaft may cause a second upper continuous track assembly to rotate independent of the first upper continuous track assembly and a second lower continuous track assembly to rotate independent of the first lower continuous track assembly, the first drive signal and the second drive signal transmitted to propel the endoscope device within the gastro-intestinal tract.

Yet another aspect of the present disclosure may include a method for manufacturing a tread for a robotic endoscopic device. The method may include the operations of injecting a first flexible material between a tubular outer mold and a first inner mold within the tubular outer mold, the first inner mold comprising a first molding surface comprising a plurality of positive micro-pattern tread pillars extending from the first molding surface, the first flexible material, when molded, comprising an outer surface and an inner surface and replacing the first inner mold with a second inner mold within the tubular outer mold, the second inner mold comprising a second molding surface comprising a plurality of positive timing-belt teeth extending from the second molding surface toward the inner surface of the first flexible material. The method may also include the operation of injecting a second flexible material between the second molding surface and the inner surface of the first flexible material, the second flexible material, when molded, comprising an outer surface comprising positive micro-pattern tread pillars extending from the outer surface and an inner surface comprising negative timing-belt teeth extending into the inner surface.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION

Figure 1:
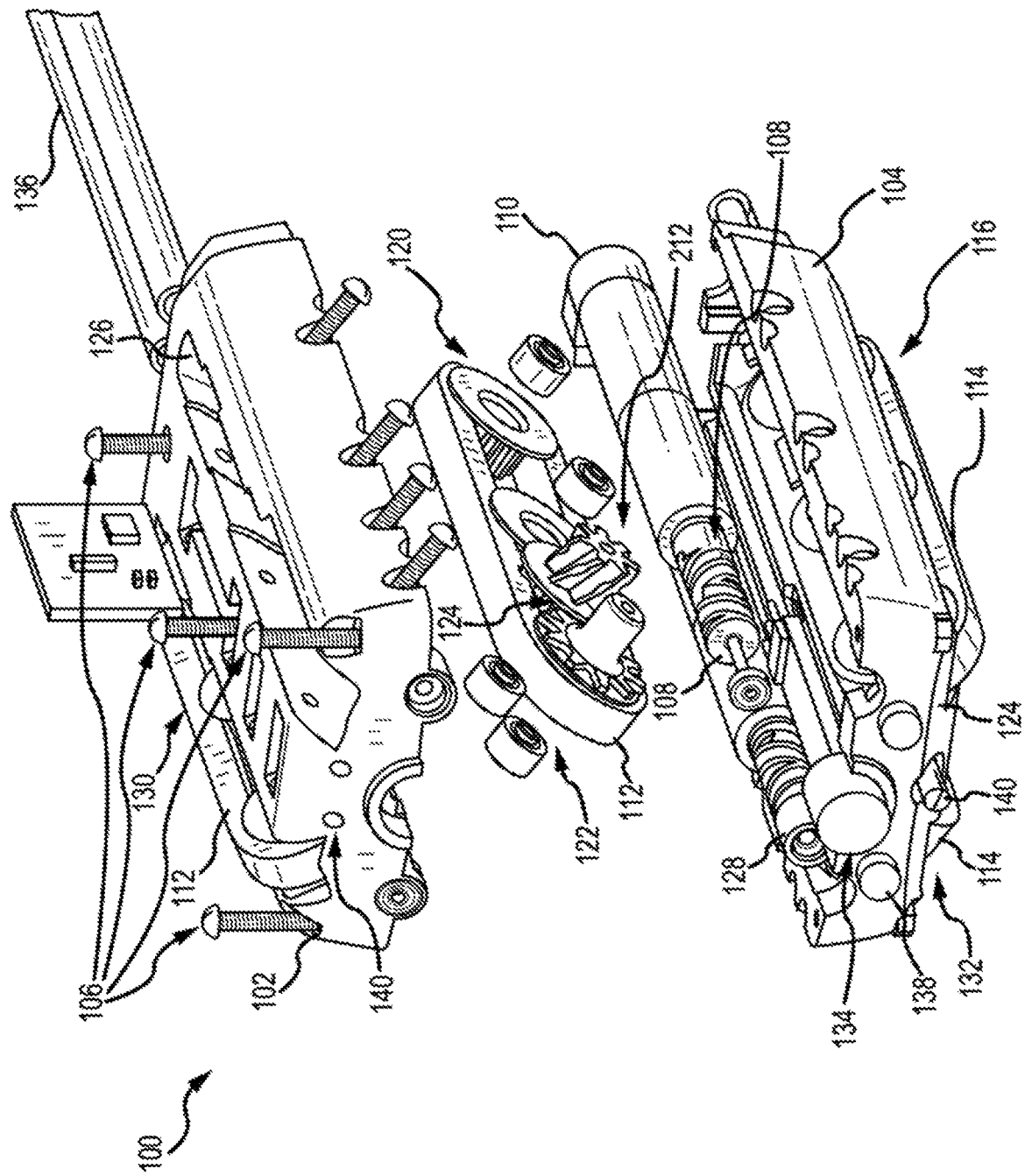
FIG. 1 illustrates an isometric, three-dimensional view of a robotic capsule endoscope according to one implementation.

Presented herein is a self-propelled semi- or fully-autonomous robotic endoscope device that would address the drawbacks of other self-propelled endoscope devices discussed above. The self-propelled robotic endoscope device may provide physicians the ability to visually diagnose, biopsy, and administer therapeutics during a single procedure to diagnosis and intervene in a wide array of gastrointestinal (GI) diseases. This includes colorectal cancers (CRCs) which remain the second most common forms of cancer and the third leading cause of cancer-related deaths in the United States. Not only does the robotic capsule endoscope discussed below reduce the technical drawbacks and risks of previous endoscope devices, but the device may also reduce time, cost, and the stigma of certain endoscopic procedures, such as colonoscopies, potentially leading to increased screening rates and fewer CRC-related fatalities.

Aspects of the present disclosure involve systems, devices, methods, and the like for a self-propelled and smart-sensing robotic capsule endoscope device that reduces procedural complexity, inherent risks, patient pain, and the overall time and cost of the frequently performed endoscopy procedure, while still containing the functionality of traditional clinical endoscopes. Although discussed herein in relation to colonoscopy procedures, it should be appreciated that the robotic capsule device may be utilized in many types of endoscopic procedures, including but not limited to small intestine endoscopic procedures, bowl endoscopic procedures, or stomach endoscopic procedures. The device may provide autonomous features, such as internal navigation, internal mapping (to localize, chart progress throughout time, and to ensure a full inspection of the mucosa during a procedure), disease detection, target-tracking and disturbance rejection for therapeutic intervention (e.g., biopsy, polypectomy, etc.), autonomous intervention, and decision making (e.g., deciding when to biopsy, re-investigate certain areas, when to alert physician of issues).

The robotic capsule endoscope presented herein may be multi-degrees of freedom and sensor-enabled for endoscopic procedures, such as a colonoscopy procedure. The device may include a "double-worm" drive that removes axial gear forces while reducing radial moments over previous robotic endoscope devices. The full parameterization of gear geometries thereby allows for robotic capsule minimization via an optimization routine over the design constraints. Two independently controlled motors may be configured to drive micro-pillared treads above and below the device, allowing for 2-degrees of freedom (DOF) skid-steering even in a collapsed lumen. The robotic device contains similar functionality of a traditional endoscope, such as a camera, adjustable LEDs, channels for insufflation and irrigation, and a tool port for common endoscopy instruments (e.g., forceps, snares, etc.). Additionally, the robotic device may include an inertial measurement unit, magnetometer, motor encoders, motor current sensors, and the like to aid in future autonomy strategies.

Figure 2:
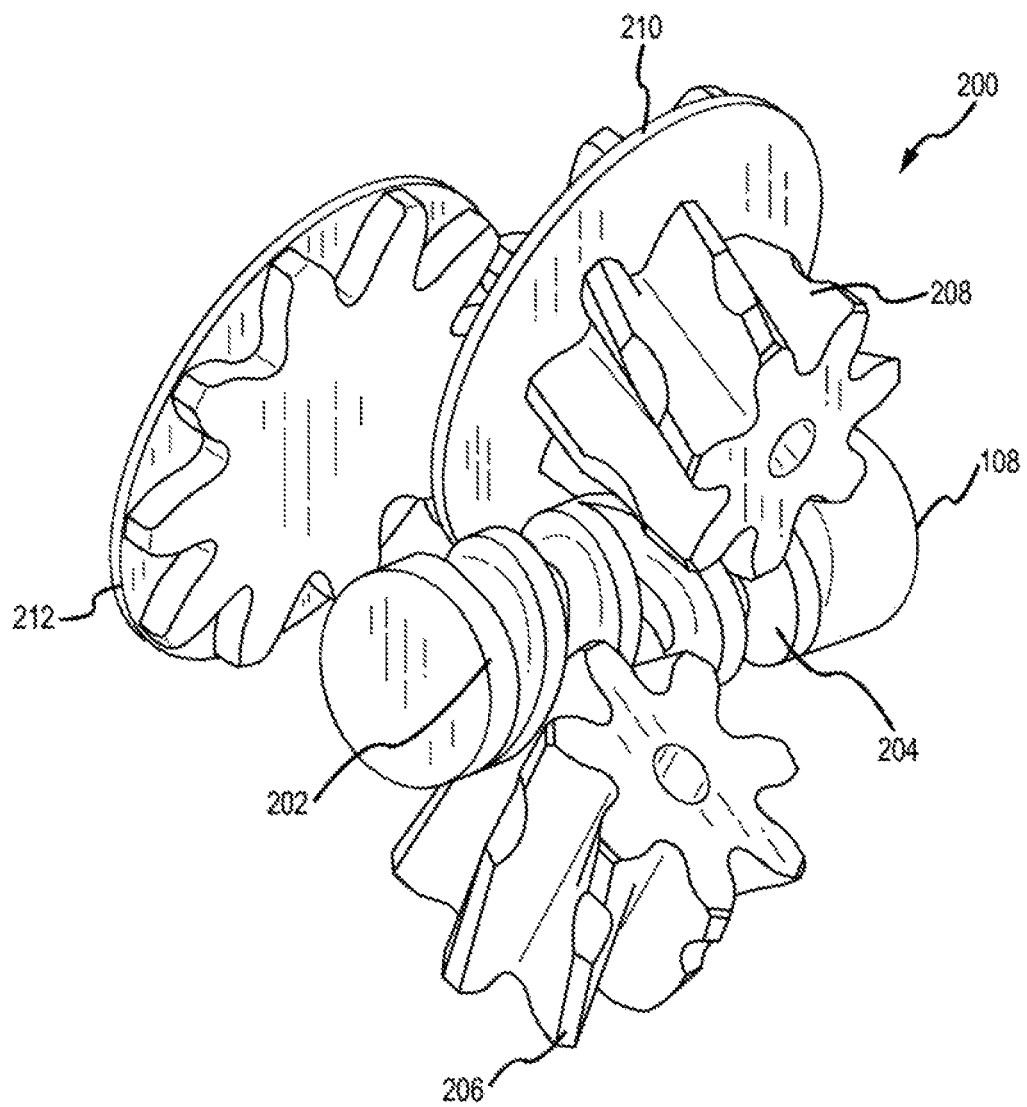
FIG. 2 illustrates an isometric view of a double worm drive mechanism with spur gear idling.

FIG. 1 illustrates an isometric, three-dimensional view of a robotic capsule endoscope 100 according to one implementation. As shown, the robotic capsule 100 may include a housing comprising an upper portion 102 and a lower portion 104. The upper portion 102 and the lower portion 104 may be fastened together in multiple locations by the machine screws 106, which provided clamping force to hold the upper portion 102 and the lower portion 104 together and the components within the housing. A first worm support shaft 108 may be disposed within the housing between the upper portion 102 and the lower portion 104. A motor 110 may be located on an end of the first worm support shaft 108 to rotate the shaft based on one or more control signals received at the motor. In some instances, the first worm support shaft 108 may include a first screw section comprising right-handed spiraling and a second screw section comprising left-handed spiraling. For example, FIG. 2 illustrates an isometric view of a double worm drive mechanism 200 with spur gear idling. As shown in the illustration, the first worm support shaft 108 includes a first portion including right-hand spiraling 202 and a second portion including left-hand spiraling 204. Rotation of the first worm support shaft 108 causes a corresponding right-handed spiraling of the first portion 202 and a left-handed spiraling of the second portion 204.

A first worm gear 206 may be engaged with the right-handed spiraling 202 of the first worm support shaft 108. As illustrated, a counter-clockwise rotation of the first worm support shaft 108 caused by the motor 110 may cause a corresponding counter-clockwise rotation of the first worm gear 206. Similarly, a second worm gear 208 may be threadably engaged with the left-handed spiraling 204 the double worm drive shaft 108. The same counter-clockwise rotation of the first worm support shaft 108 discussed above may cause a corresponding counter-clockwise rotation of the second worm gear 208.

To achieve the overall shape of the cylindrical capsule-shaped robot 100 (i.e., longer than it is wide), the motor 110 may be parallel to the treads 112, 114 (discussed in more detail below) that are powered by the motor 110. In one implementation, a 90-degree power transmission from cylindrical DC motors 110 may be utilized. Further, to reduce gear forces and generate the smallest possible space claim, the first worm support shaft 108 is used. A single worm drive shaft can transmit power to multiple worm gears 206, 208, and thus a single motor 110 can drive the top tread 112 and bottom treads 114 in the same rolling direction. In instances where the worm gears are of the same right-handed spiraling and mirrored about the drivetrain (i.e., driving at the same angle to the surface), the worm gears produce a planar resultant force angled toward either top or bottom and a doubled axial force. However, this favoring of a top or bottom gearset and doubled axial force on the motor 110 is generally not conducive to a drivetrain of the size used in the capsule robot 100, as it necessitates additional thrust and radial bearing support. To conserve space and reduce complexity, the "double-worm" drive discussed above is used that includes both right-hand 202 and left-hand spiraling 204. With opposite handed worm gears interacting on a single screw, the radial force no longer favors top or bottom gears and instead is directed inward or outward on the mirroring plane (see FIG. 2, right). Additionally, the resultant axial force is eliminated, reducing motor strain.

Figure 3:
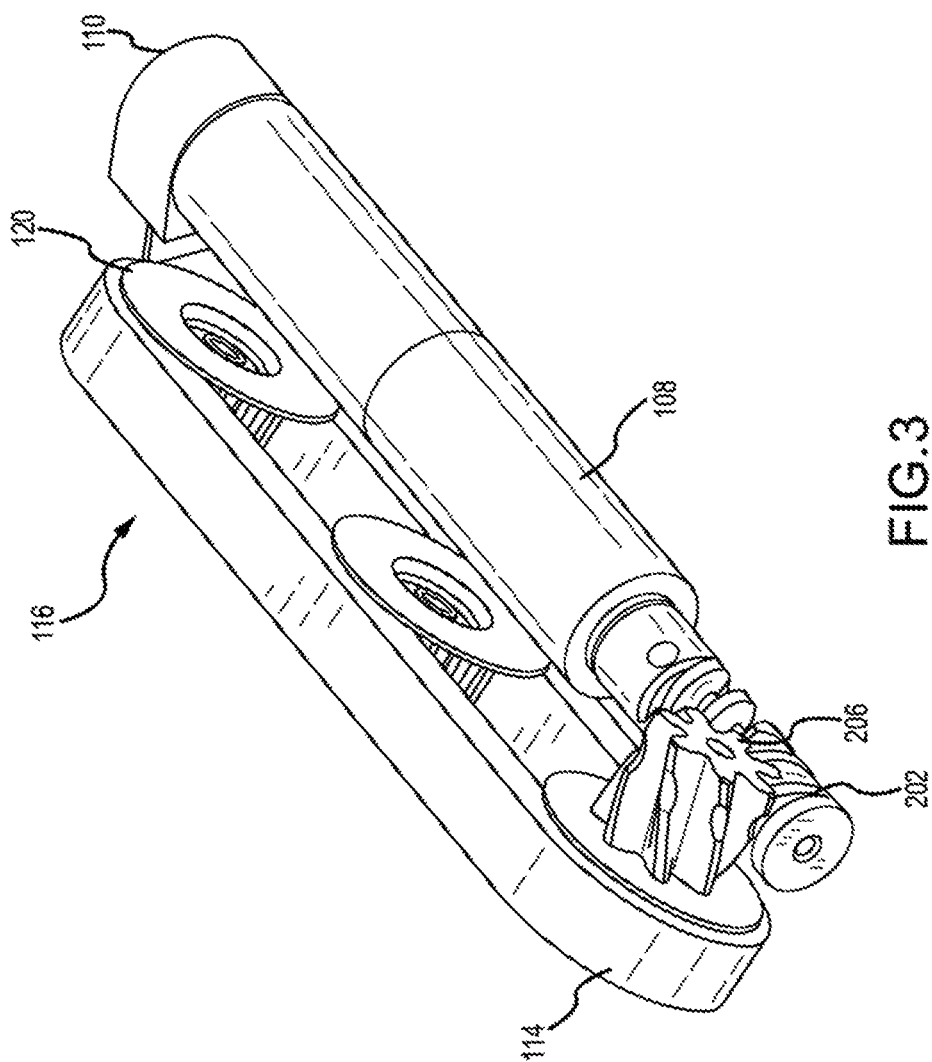
FIG. 3 illustrates an isometric view of a continuous track assembly threadably engaged with the double worm drive shaft to rotate a tread or track to propel the capsule robot.

Returning to FIG. 1 and FIG. 2, the first worm gear 206 in threadably engaged with the right-handed spiraling 202 of the first worm support shaft 108 such that a counter-clockwise rotation of the first worm support shaft caused by the motor 110 may cause a corresponding counter-clockwise rotation of the first worm gear 206. In a similar manner, a clockwise rotation of the first worm support shaft 108 may cause a corresponding clockwise rotation of the first worm gear 206. The first worm gear 206 may thus be utilized to drive a rotation of a lower continuous track assembly 116. In particular, FIG. 3 illustrates an isometric view of a continuous track assembly 116 threadably engaged with the double worm drive shaft 108 to rotate a tread or track 114 to propel the capsule robot 100. The continuous track assembly 116 may include the first worm gear 206, one or more pulley gears 120, and a continuous track 114 driven by the rotation of the first worm gear 206 about the one or more pulley gears 120. For example, motor 110 may, in some instances, rotate the first worm support shaft 108 in a counter-clockwise direction about the shaft axis. Through the right-handed spiraling 202, first worm gear 206 similarly rotates in a counter-clockwise direction. Tread 114 may similarly rotate in a counter-clockwise in response to the rotation of the first worm gear 206. As shown in FIG. 1, the treads 114 may extend from the lower portion 104 of the housing through a first angled continuous track slot 124 included in the lower portion of the housing. The angled continuous track slot allow for a portion of the lower continuous track assembly 116 to extend from the lower portion 104 of the housing to engage with a surface, such as an inside surface of a GI tract. The rotation of the treads 114 of the continuous track assembly 116 in this direction may thus propel the robotic capsule in a first direction through the activation of the motor 110 and rotation of the first worm support shaft 108.

Although the double worm drive concept with opposite handed gear interactions produces favorable forces, the top treads 112 and bottom treads 114 will no longer rotate in the same rolling direction (as best seen in FIG. 2). That is, if the bottom treads 114 are rolling the device 100 forward, the top treads 112 would be attempting to roll it backward, thus causing the device to retroflex instead of propelling it in a single direction. Thus, the capsule robot 100 may include one or more idler gears 210, 212 into an upper continuous track assembly 122, thereby regaining similar rolling directions for both the lower treads 114 and the upper treads 112.

In particular and with reference to FIG. 2, an idler gear 212 may be threadably engaged with the second worm gear 208 to reverse the direction of rotation transmitted to the upper continuous track assembly 122. The idler gear 212 may engage a spur mesh 124 of the second worm gear 208. The idler gear 212 may be engaged with an upper continuous track assembly 122 similar to the lower continuous track assembly 116 discussed above. As in a similar manner, the idler gear 212 transmits rotation of the second worm gear 208 to rotation of an upper continuous track assembly 122 in a direction opposite of the direction of the lower continuous track assembly. For example, motor 110 may, in some instances, rotate the first worm support shaft 108 in a counter-clockwise direction about the shaft axis. Through the left-handed spiraling 204 of the first worm support shaft 108, second worm gear 208 similarly rotates in a counter-clockwise direction. However, rotation of the upper continuous track assembly 122 in a counter-clockwise direction would cause the upper treads 112 to drive the capsule robotic device 100 backward, or in the opposite direction of the lower treads 114. Thus, idler gear 212 may translate the counter-clockwise rotation of the second worm gear 208 into a clockwise rotation. This clockwise rotation may be transmitted to the upper continuous track assembly 122 in a similar manner as described above. As shown in FIG. 1, the treads 112 of the upper continuous track assembly 122 may extend from the upper portion 102 of the housing through a corresponding slot 126 in the upper portion 102. The rotation of the treads 112 of the continuous track assembly 120 in this direction may, in conjunction with the rotation of the lower treads 114, propel the robotic capsule 100 in a first direction. In this manner, the double worm drive shaft 108 may drive both of the upper continuous track assembly 122 and the lower continuous track assembly 116 simultaneously while addressing the forces discussed above.

In some embodiments, the treads 112, 114 of the continuous track assemblies 116, 122 may include micropillared polydimethylsiloxane (PDMS) timing-belt style treads. The micropillared PDMS treads may be used in response to the slippery, mucosa surface upon which the capsule robotic device 100 is deployed. Further, a slight angle is provided for the continuous track assemblies 116, 122 to improve traction on the surface of the environment in which the device 100 is deployed. For example, rather than a flat planar surface that conventional vehicles encounter, the colon mucosa, although variable, is often elliptical or semi-rounded in nature. Providing the continuous track assemblies 116, 122 on a slight angle may improve the traction on such irregular, deformable surfaces.

In some embodiments, a second motor (not shown) and a second worm support shaft 128 may be included to drive a second upper continuous track assembly 130 and a second lower continuous track assembly 132. The operation and design of the second upper continuous track assembly 130 and a second lower continuous track assembly 132 may mirror that described above. Thus, the second lower continuous track assembly 132 may include a first worm gear threadably engaged with a right-hand spiraled section of the second worm support shaft 128 to transmit rotation of the second worm support shaft 128 to rotation of the second lower continuous track 132. The second lower continuous track 132 may extend through an angled slot of the lower portion 104 of the housing. Similarly, a second upper continuous track assembly 130 may include a second worm gear threadably engaged with a left-hand spiraled section of the second worm support shaft 128 to transmit rotation of the second worm support shaft 128 to rotation of the second upper continuous track assembly 130. To alter the direction of rotation of the tread 112 of the second upper continuous track assembly 130, an idler gear may be included in the assembly as explained above. The second upper continuous track 130 may extend through an angled slot of the upper portion 102 of the housing. In some embodiments, the second angled slot of the upper portion 102 of the housing may be substantially perpendicular to the first angled slot and the second angled slot of the lower portion 104 of the housing may be substantially perpendicular to the first angled slot.

The second motor and second worm support shaft 128 provides for 2-DOF locomotion through skid-steering with independently controlled left and right treads. This has the added benefits of improving the balance of the capsule robot 100 (i.e., the heaviest components of the assembly, the motors, can be placed far from the center of gravity) and allowing for an increased turning moment. Each of these motors may power treads above and below the capsule robot 100 allowing for omni-directionality may be useful in a collapsed lumen, which is the natural uninflated state of the intestine.

One or more additional features or devices may be included in or on the capsule robotic device 100 for use in colonoscopy procedures. For example, a camera device 134 may extend from a front portion of the housing for collecting video or photographs during a procedure in which the capsule robot device 100 is used. Information obtained by the camera, such as a live video feed, may be transmitted to a display device for analysis by a technician. One or more lighting devices 138, such as a light-emitting diode (LED), may be included in the device 100 to provide lighting for video and/or photography by the camera 134.

In one example, the robotic device 100 may be untethered and include wireless capabilities to provide the video feed. In another example, a wire may be included in a flexible tether that extend from the rear of the device 100. The flexible tether may house any number and type of wires, tubes, or other transporting media for use by the robotic device 100. The wires housed in the tether may be connected to a video processing device and/or display for use by a technician during a colonoscopy procedure. In another example, the tether may house one or more motor control wires for transmitting control or activation signals to the motors 110 of the capsule device 100. Through transmission of control signals to the motor 110 along the tether, the movement of the capsule robotic device 100 may be controlled.

The tether may also include an air tube, a water tube, or a combination of air and water tubing 136. The air/water tubing 136 may transport air (for inflation of an intestine) and/or water (for cleansing of an area) during a procedure. One or more air/water channels/spouts 140 may be located on the front of the device 100 to provide for delivery of the air/water carried on the air/water tubing 136. A tool port 140 may also be disposed on the front portion of the device 100 for activation of one or more tools associated with a colonoscopy procedure. For example, a forceps tool may be integrated with the tool port 140 for collecting biopsies during a procedure. The forceps may be controlled through the tool port 140, which may include a control line housed within the tether trailing the robotic device 100. Control signals transmitted on the control line may activate one or more tools integrated with the tool port 140. Other tools may also be used with the device 100, including snares, tattoo needles, and the like). Additional autonomous features, such as colon navigation, internal mapping (to localize, chart progress throughout time, and to ensure a full inspection of the mucosa during a procedure), disease detection, target-tracking and disturbance rejection for therapeutic intervention (e.g., biopsy, polypectomy, etc.), autonomous intervention, and decision making (e.g., deciding when to biopsy, re-investigate certain areas, when to alert physician of issues) may also be implemented through control of the capsule robotic device 100.

Many parameters of the design of the capsule robotic device 100 may be considered in selecting the components and design of the device. For example, a high-level analysis of run-out speed and rimpull may be calculated to determine a proper motor gearhead reduction. The motors chosen for one particular capsule robotic design may include six possible planetary gearhead torque ratios: 4:1, 16:1, 64:1, 256:1, 1024:1, and 4096:1. To determine the maximum possible run-out speed and rimpull of each of these gearhead combinations, assumptions may be made for the rest of the drivetrain, specifically the tread rolling radius and worm drive torque ratio. The tread rolling radius, using 0.080" MXL timing pulley teeth, was assumed between 4.23 and 7.85 mm (i.e., a minimum of 10 pulley teeth/1 mm thick treads, versus a maximum of 15 pulley teeth/3 mm thick treads), and the worm torque ratio, at full efficiency, was assumed between 2 and 20 (i.e., a minimum of 8 gear teeth/4 worm leads, versus a maximum of 20 gear teeth/1 worm lead). From these assumptions, maximum and minimum rolling speed and tractive wheel force may be calculated by:

$$V_{MAX} = \frac{\omega MAX}{N_{gh}N_w}R$$

$$F_{MAX} = 2\frac{T_{MAX}N_{gh}N_w\eta_{gh}}{R}$$

where $N_{gh}$ is the gearhead torque ratio, $N_w$ is the worm drive torque ratio, and R is the rolling radius. The motor and gearhead run-out speeds, stall torques, and efficiencies, $\omega_{MAX}$, $T_{MAX}$, and $\eta$, respectively, are given by specifications of the motor 110. There is a multiplying factor of 2 in the rimpull equation because two motors are utilized in the capsule robotic design 100.

The drivetrain has a theoretical maximum run-out speed of 4.3 mm/s, assuming no significant rolling friction losses, with a theoretical stall rimpull was 29.6 N, not including losses from drivetrain friction. Thus, to assure adequate rimpull without sacrificing speed, the 64:1 gear ratio may be chosen. Other ratios, such as 256:1 gearhead may also be chosen to supply ample torque and speed, but higher ratio gearheads typically add length and decrease efficiencies.

Design of the double worm drive shaft 108, 128 may include designs for: worm screw leads ($n_w$), worm gear teeth ($n_{wg}$), lead angle ($\alpha$), pressure angle ($\varphi$), tooth module (m), and tooth sliding coefficient of friction ($\mu_w$). These terms may be used to calculate the worm drive's efficiency ($\eta_w$), speed ratio ($M_w$), and torque ratio ($N_w$) through the relations:

$$\eta_w = \frac{\cos\varphi - \mu_w\tan\alpha}{\cos\varphi + \mu_w\cot\alpha}$$

$$M_w = \frac{\eta_w}{\eta_{wg}}$$

$$N_w = \eta_w\frac{\eta_{wq}}{\eta_w}$$

In addition, the design of the components of the device 100 may be such that the gear teeth do not yield during operation. With the gear parameters previously mentioned and knowledge of the drivetrain (i.e., motor/gearhead torque and material strength), the gear tooth bending safety factor (SF) can be calculated. This stems from worm force calculations, as each gear tooth experiences a reactive force during operation and creates a maximum cantilever stress at the base of each gear tooth. After simplification of the forces created by the gearhead output torque ($T_{gh}$), the normal force tangent to a worm lead/worm gear tooth (i.e., the maximum resultant force at the tip of each tooth) can be calculated as:

$$F_{t,max} = \cos\varphi\frac{\tau_{gh,max}/\left(\frac{mn_w}{2\tan\alpha}\right)}{\cos\varphi\sin\alpha + \mu_w\cos\alpha}$$

The previously mentioned parameters of worm drive design, along with additional parameters of tooth addendum/dedendum length and tooth width, fully define the geometry of each gear tooth. Thus, by knowing the maximum tangential force applied to the tip, as well as the tooth height ($h_t$), thickness ($t_t$), and width ($w_t$), the maximum cantilever stress may be calculated as:

$$\sigma_{max} = \frac{6F_{t,max}h_t}{w_t t_t^2}$$

and therefore the safety factor is fully parameterized by the following relation to the gear's material yield strength ($\sigma_y$):

$$SF = \frac{\sigma_y}{\sigma_{max}}$$

The geometry of the drivetrain may also be parameterized based on assumed hardware. FIG. 3 depicts the variables present in designing a worm pair interaction with a pulley attached to the end of the worm gear. This parameterization will allow for optimization over geometric constraints such as preventing interferences and keeping adequate clearance between parts.

The simplified equations above may be used in a generalized reduced gradient (GRG) nonlinear optimization routine with given parameter/design constraints. Both the height and width variables may be each individually used as the objective functions, with particular emphasis on minimization of the device width. Due to the idling gear interaction for the double-worm, similar gear safety and clearance calculations may be used to create a 1:1 ratio spur gear mesh on one side of the robot device 100.

With the drivetrain minimized in size, additional surgical tools, features, and sensing hardware could be fit into gaps within the housing of the capsule robotic device 100. For example, vision, lighting, insufflation channel, water channel, and a channel for multiple endoscopic tools (e.g., biopsy forceps, snares, tattoo needles, etc.) may all be incorporated into the housing of the device 100. For example, a 5.5 mm diameter camera 134 with six internal 1 mm rectangular LEDs, two additional round white 3 mm LEDs 138, two 1.52 mm air/water channels 140 fed by ⅛" external diameter silicone tubing 136, and a ⅛" diameter channel for tool overtubes 140 may be incorporated into the device 100.

Additionally, the capsule robotic device 100 may incorporate electronic sensing capabilities. For example, a progressive-scanning CMOS camera may be modified from an off-the-shelf otoscope by modifying the lens/housing to allow for a more appropriate focal length, approximately 3 inches in front of the robot 100. This USB-connected camera may enable the setting of a manual exposure time and fixed frame rate, facilitating future image processing. For inertial and pose sensing, a 6-DOF inertial measurement unit (IMU) with a 3-DOF magnetometer may be designed to fit within the device 100. To better observe and control the motors 110, dual channel encoders may be present onboard the device's two motors 110, and an octal current/voltage sensor may be implemented externally on a printed circuit board (PCB) to read current draw from each motor over a connection.

Figure 4:
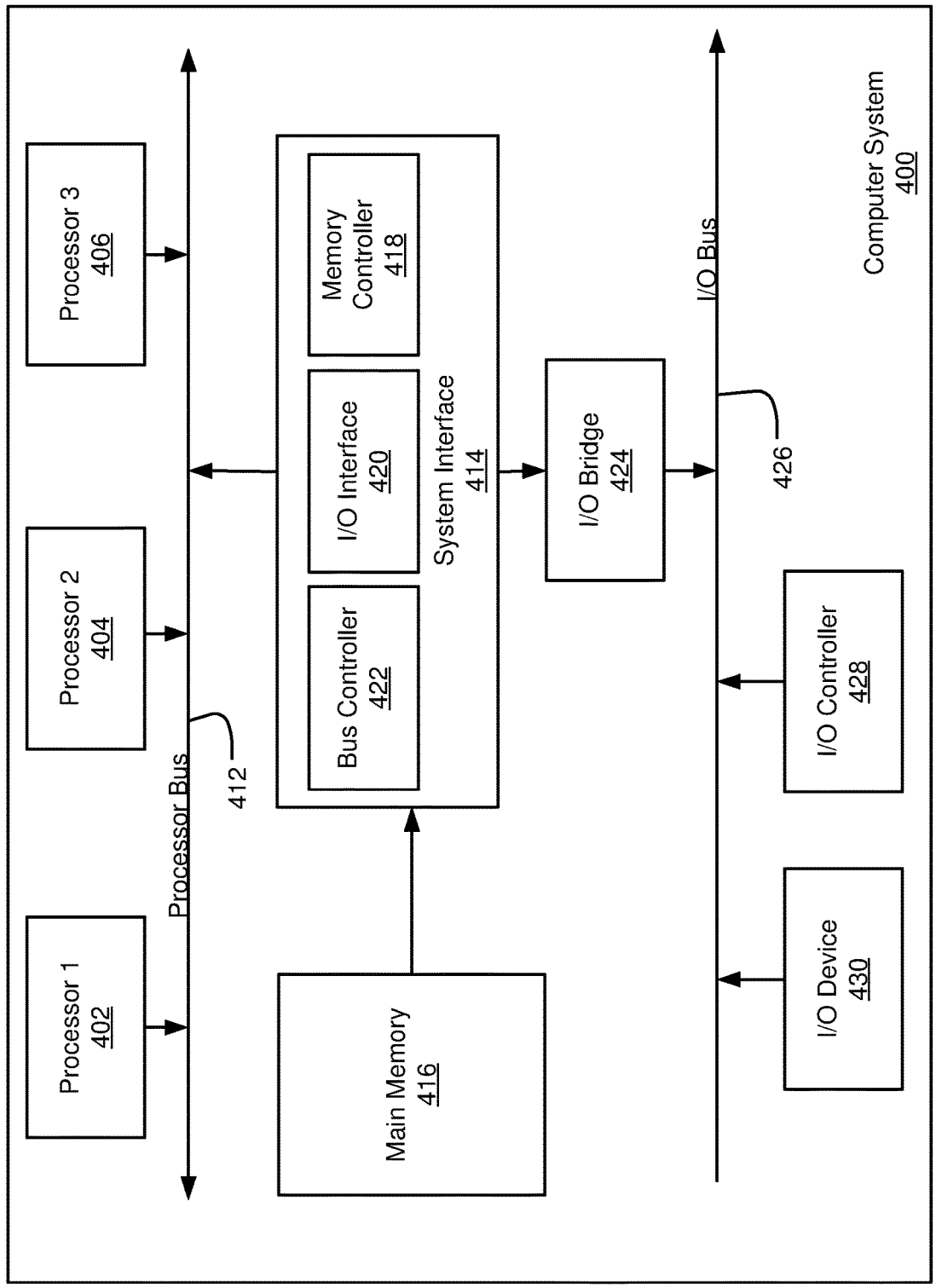
FIG. 4 is a diagram illustrating an example of a computing system which may be used in implementing embodiments of the present disclosure.

In some embodiments, an offboard computing device may be used to control features of the capsule robotic device 100, such as through generation and transmission of control signals to the motors of the device to control the movement of the device. FIG. 4 is a block diagram illustrating an example of such a computing device 400 which may be used in controlling the embodiments of the device discussed herein. The computer system (system) includes one or more processors 402-406. Processors 402-406 may include one or more internal levels of cache (not shown) and a bus controller or bus interface unit to direct interaction with the processor bus 412. Processor bus 412, also known as the host bus or the front side bus, may be used to couple the processors 402-406 with the system interface 414. System interface 414 may be connected to the processor bus 412 to interface other components of the system 400 with the processor bus 412. For example, system interface 414 may include a memory controller 414 for interfacing a main memory 416 with the processor bus 412. The main memory 416 typically includes one or more memory cards and a control circuit (not shown). System interface 414 may also include an input/output (I/O) interface 420 to interface one or more I/O bridges or I/O devices with the processor bus 412. One or more I/O controllers and/or I/O devices may be connected with the I/O bus 426, such as I/O controller 428 and I/O device 430, as illustrated.

I/O device 430 may also include an input device (not shown), such as an alphanumeric input device, including alphanumeric and other keys for communicating information and/or command selections to the processors 402-406. Another type of user input device includes cursor control, such as a mouse, a trackball, or cursor direction keys for communicating direction information and command selections to the processors 402-406 and for controlling cursor movement on the display device.

System 400 may include a dynamic storage device, referred to as main memory 416, or a random access memory (RAM) or other computer-readable devices coupled to the processor bus 412 for storing information and instructions to be executed by the processors 402-406. Main memory 416 also may be used for storing temporary variables or other intermediate information during execution of instructions by the processors 402-406. System 400 may include a read only memory (ROM) and/or other static storage device coupled to the processor bus 412 for storing static information and instructions for the processors 402-406. The system set forth in FIG. 4 is but one possible example of a computer system that may employ or be configured in accordance with aspects of the present disclosure.

According to one embodiment, the above control signals may be generated by computer system 400 in response to processor 404 executing one or more sequences of one or more instructions contained in main memory 416. These instructions may be read into main memory 416 from another machine-readable medium, such as a storage device. Execution of the sequences of instructions contained in main memory 416 may cause processors 402-406 to perform the process steps described herein. In alternative embodiments, circuitry may be used in place of or in combination with the software instructions. Thus, embodiments of the present disclosure may include both hardware and software components.

A machine readable medium includes any mechanism for storing or transmitting information in a form (e.g., software, processing application) readable by a machine (e.g., a computer). Such media may take the form of, but is not limited to, non-volatile media and volatile media and may include removable data storage media, non-removable data storage media, and/or external storage devices made available via a wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, SSDs, and the like. The one or more memory devices 606 may include volatile memory (e.g., dynamic random access memory (DRAM), static random access memory (SRAM), etc.) and/or non-volatile memory (e.g., read-only memory (ROM), flash memory, etc.).

Computer program products containing mechanisms to effectuate the systems and methods in accordance with the presently described technology may reside in main memory 816, which may be referred to as machine-readable media. It will be appreciated that machine-readable media may include any tangible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

In some instances, a custom offboard PCB may be used to control the device 100. The custom PCB may contain most of the necessary hardware for controlling the device, including a small Wi-Fi enabled device serving as the onboard processing and communications unit for the device 100. The PCB may utilize a microcontroller to send and interpret digital and analog input/output signals. Commands and data to/from the device 100 may be sent via a serial connection to/from a communications interface. The PCB may control the robotic device's 100 two motors 110 via a PWM controlled dual motor driver. To allow for efficient power distribution to the Photon, two switching voltage regulators may be used to step down the input voltage to 5 V and 3.3 V, respectively. This also allows the direct current (DC) motors to be powered at up to 9 V without risking damage to other onboard hardware.

The camera and microcontroller may both connect via USB to a computing device and a simple graphical user interface (GUI) may provide a way to both send commands and display/collect data over the serial port. User inputs may control motor speed, LED brightness, and to set device modes and data collection. Onboard data from the capsule robotic device 100, including an encoder, inertial measurement unit (IMU), current and camera data may all be collected and displayed and saved to file via the GUI, while control commands may be passed to the device 100 while also being saved to the data file.

In one instance, the gear components may be 3-D printed with material on a 3-D printer device. The case top and bottom pieces may be fastened together in multiple locations by the same machine screws and nuts, which provided clamping force to hold the motors in place. The double-worm components may be supported by a 1 mm steel shaft pressed into a 3 mm diameter ball bearing affixed to the case. The camera, IMU, and LEDs may be first conformal coated (to prevent damage in the wet colon environment) and then wired to a 2 m tether before being glued in place within the cases. Finally, tubing for air, water, and tools may be affixed to the case's ports.

Figure 5:
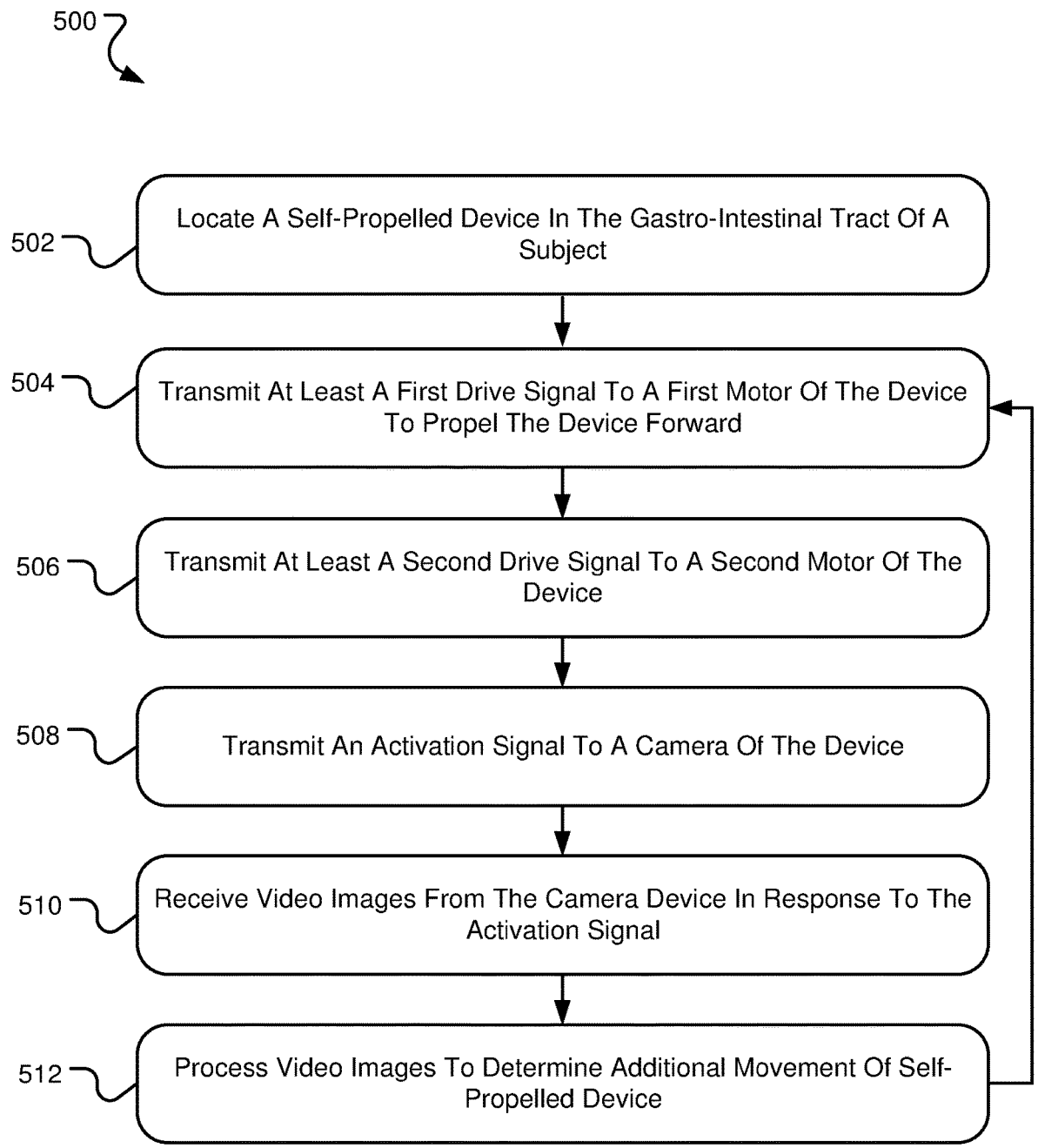
FIG. 5 is a flowchart illustrating a method for controlling a capsule robotic device for an endoscopy procedure.

FIG. 5 is a flowchart illustrating a method 500 for controlling a capsule robotic device for a colonoscopy procedure. The method 500 may be performed by one or more technicians, physicians, computing devices, and the like to perform such a procedure as a colonoscopy. As such, one or more of the operations of the method 500 may be performed manually by the physician or through providing inputs to a computing device to control a capsule robotic device 100, such as the device described herein.

Beginning in operation 502, a self-propelled robotic device 100 may be located in the gastro-intestinal tract of a subject. In one example, the device 100 may be located in the gastro-intestinal tract of a subject to perform or during a colonoscopy procedure. In operation 504, a computing device may be utilized to transmit at least one first drive signal to a first motor of the device to propel the device forward within the GI tract. As described above, the device 100 may include two motors controlling two double worm drive shafts independently. A first double worm drive shaft may cause a first upper continuous track assembly to rotate in a first direction and a first lower continuous track assembly to rotate in a second direction opposite the first direction in response to the first drive signal, as discussed above. In some instances, a second drive signal may be transmitted to the other motor in operation 506 to aid in the forward propulsion of the self-propelled device through rotation of a second upper continuous track assembly and a second lower continuous track assembly.

In still other instances, the second drive signal transmitted to the second motor may drive the second double worm drive shaft in an opposite rotation to that of the first double worm drive shaft to cause the second upper continuous track assembly and a second lower continuous track assembly to rotate in the opposite direction as the first upper continuous track assembly and the first lower continuous track assembly. Through this combination of drive signals, the device 100 may perform a skid-steer or 0-degree turn. For example, the upper and lower continuous track assemblies on the left side of the device 100 may be driven in a forward direction while the upper and lower continuous track assemblies on the right side of the device 100 may be driven in a reverse direction. The coinciding movements of the left-side track assemblies and the right-side track assemblies may cause the device 100 to perform a skid-steer right turn. As such, the independent control over the left and right-side track assemblies provides additional control over the movement of the device than devices that include a single drive shaft.

In operation 508, a camera activation signal may be transmitted to the device to begin collecting images from the camera. In some instances, the activation signal may be provided through a wireless connection to the camera. In another instances, a tether extending from the rear of the device 100 may house an electrical wire through which the activation signal is transmitted to activate the camera. In still other instances, the activation signal may be generated onboard the robotic device 100 from a CPU located or adjacent the device. For example, the robotic device 100 may include a CPU or other processing device to perform navigation decisions, processing decisions, activation decisions, and the like. In addition, the captured images may be provided to a computing device or display device in operation 510. The captured images may similarly be transmitted via a wireless connection or via one or more conducting wires of the tether. In a similar manner, other controllable elements of the device 100 may be controlled through one or more activation signals transmitted to the device. For example, one or more lights, other sensors, collecting devices, tools, etc. may be activated through a control signal transmitted to the device. In some instances, the activation signal may activate an air spout or water spout to deliver air or water into the GI tract.

In operation 512, the video images, or any feedback information from the robotic capsule device 100, may be processed to determine additional movements of the self-propelled device. For example, the video images may indicate that an obstruction is in front of the device 100. The device 100, an operator of the device, a controller or computing device in communication with the device, or any other processing system may determine the device should be turned in one direction or another based on the obstruction in front of the device. Processing of the images may be accomplished through image processing by a computing device, the robotic device, or through an administrator/physician controlling the device. Based on the processing of the images, additional drive signals may be transmitted to the device 100, as indicated in the flowchart 500 returning to operation 504 to repeat the above operations.

The capsule robotic device 100 and method of using the device described herein may provide several benefits over previous colonoscope devices. For example, the double-worm gear design may provide reduction of gear forces, movement of two separate gears in two directions, driving the device 100 from bottom or top of the device. Further, custom parameterization of variables allows for significant space-claim minimization as compared to other methods of gearings (spur gears, bevel gears, planetaries, etc.) and the device 100 is non-backdriveable, improving safety of the device. In addition, the device 100 has two DOF (can drive fwd/rev and skid-steering turning) due to the two independently controlled motors on left and right sides. Additionally, the gear mechanism described above allows for top and bottom tread of each independent side to be driven in tandem, thus the top and bottom of one motor side drive together and in the same direction. This provides multi-DOF skid-steering (i.e., like a tank) allowing 0-point turns (i.e., turns on the spot) which is helpful to navigation in a tight enclosed space such as the colon. The two independent motors allow for more controllability of the robot device 100, beneficial for autonomous procedures. The angled treads allow for increased surface area and tractive force on a nonplanar and deformable surface such as the colon and the robot is "flappable", i.e., can be flipped over and drive in the same manner, which is necessary for a 3D treacherous environment such as the colon, which helps if the device accidentally flips, the user decides to flip the robot to change its workspace/view/lighting, a tread is damaged/broken or other hardware fails and the device still needs to be driven safely, and/or the colon collapses.

Figure 6:
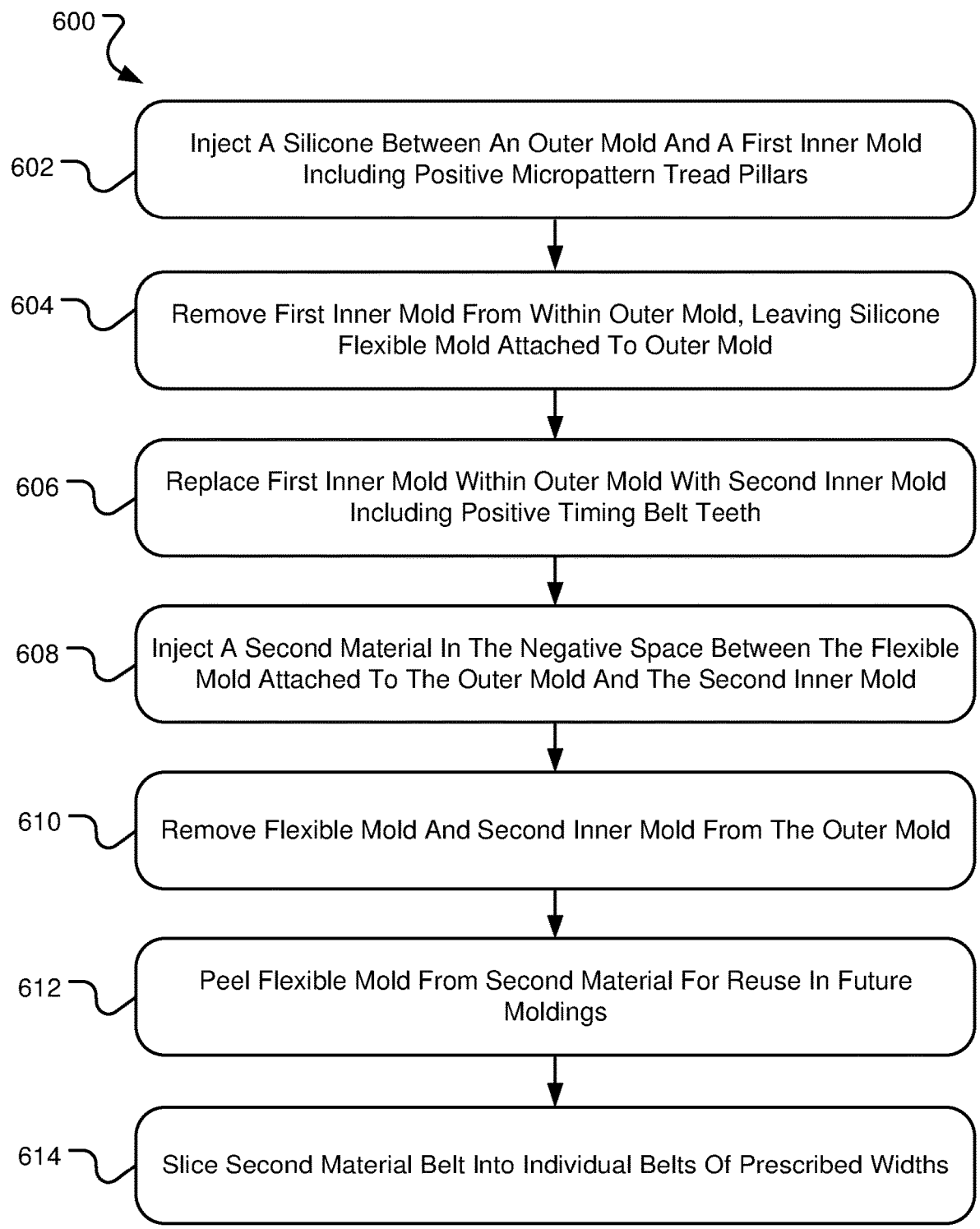
FIG. 6 is a flowchart illustrating a method to generate a tread with inner timing-belt teeth and outer micropatterns from material having tunable elasticity for micropattern performance.
Figure 7:
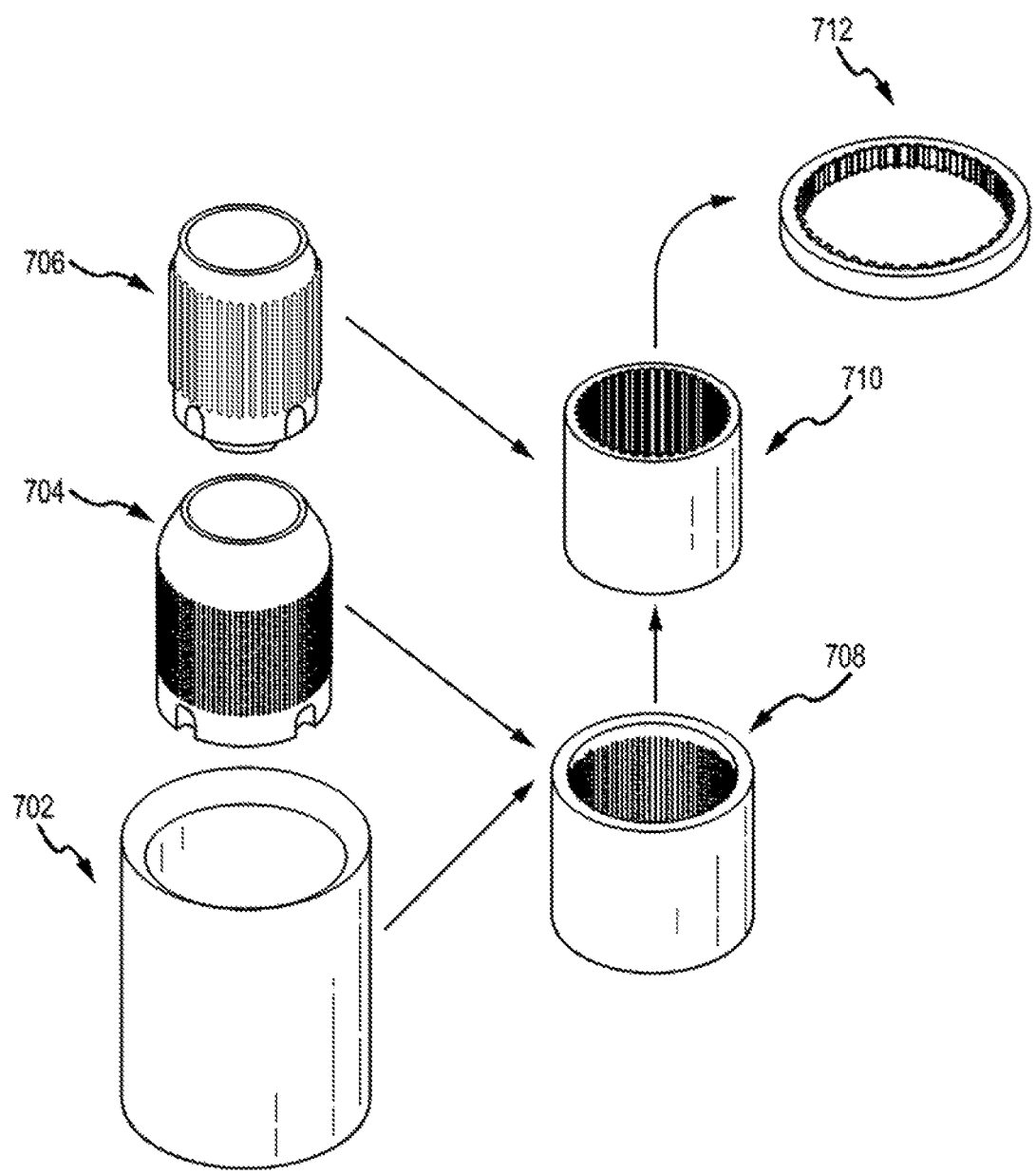
FIG. 7 is a diagram illustrating molds utilized to generate the tread with inner timing-belt teeth and outer micropatterns.

The continuous timing belt tread assembly may also provide additional benefits over previous devices. For example, a timing-belt is used to transfer power from the front to rear wheels/pulleys. Micropattern treads may be disposed on the outside of the tread to gain traction on the slippery colon mucosa. A process to combine inner timing-belt teeth with outer micropatterns may thus be used to create the treads from material having tunable elasticity for micropattern performance. One example of such a process is illustrated in the flowchart 600 of FIG. 6. The molds and process utilized to generate the tread through the method 600 of FIG. 6 is illustrated in FIG. 7. In particular, the molding process 600 may include a single outer mold (OM) 702, a first inner mold 704 (IM1), and a second inner mold 706 (IM2). Through process 600, the molds 702-706 may be used to create a long cylindrical tread 710, which is then cut into individual belts 712 (multiple can be made from one molding process). The first inner mold 704 (IM1) may include positive micropatterns on an outer surface and may be inserted within the outer mold 702 (OM). Silicone, or another flexible material, may injected, in operation 602, between IM1 074 and OM 702 to create a flexible mold 708 with negative micropatterns on its inner diameter. The flexible mold 708 may be left within the OM 702 and the IM1 704 is removed from the OM in operation 604. A second inner mold (IM2) 706 with positive timing belt teeth is placed within the OM 702 in operation 606. Specified elasticity PDMS, or another flexible material, is injected, in operation 608, into the negative space between the IM2 706 and the OM 702 to create a long cylindrical tread 710 with large timing-belt teeth on the inside surface and micropatterns on the outside surface. The flexible mold 708 and PDMS cylinder 710 are removed from the OM 702 together in operation 610. Further, the flexibility of the flexible mold 708 allows it to be "peeled off" the PDMS 710 without damaging the delicate micropatterns and allows it to be reused, in operation 612. The PDMS belt cylinder 710, still on the IM2 706, may then be spun at high-speed and a thin sharp razor is used to slice it into individual belts 712 of prescribed width in operation 614.

Figure 8:
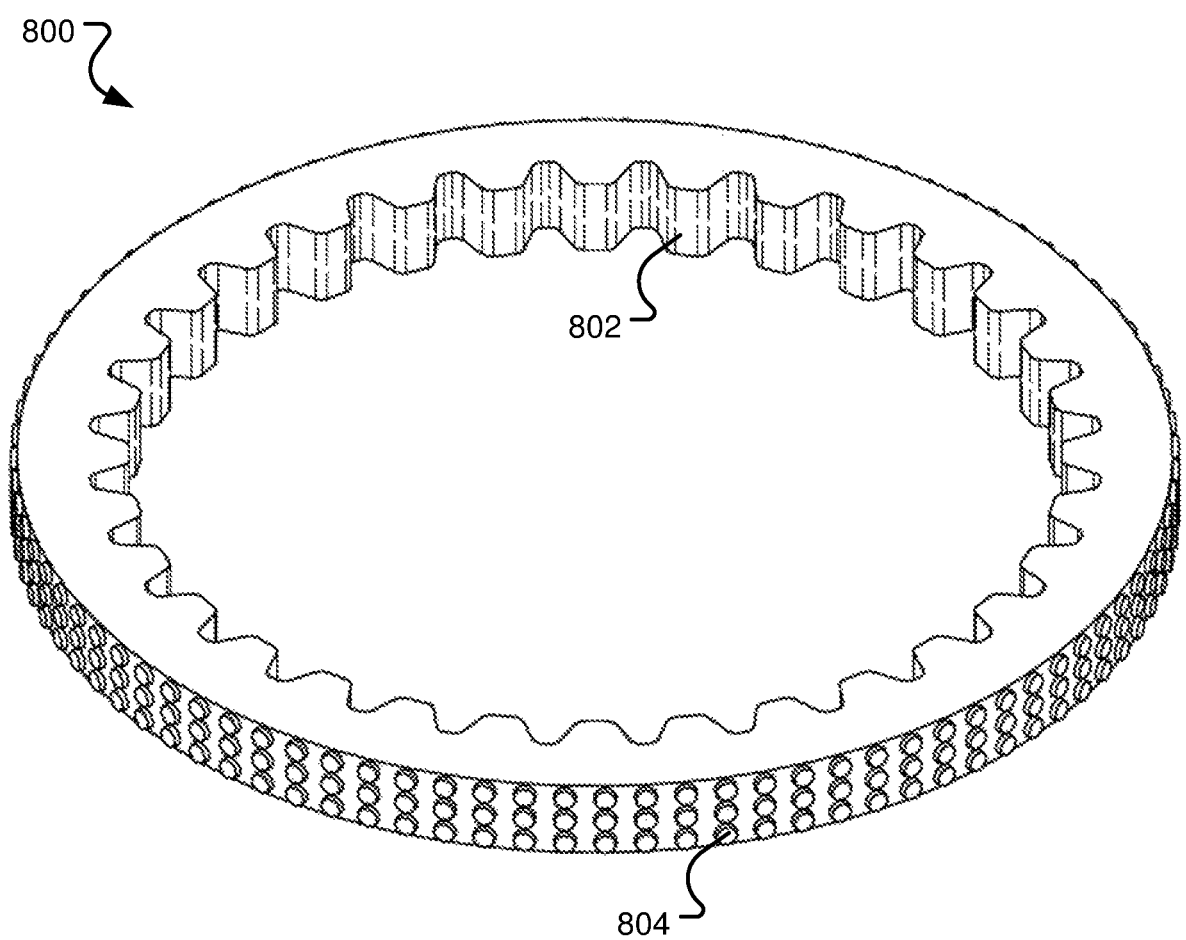
FIG. 8 is a diagram of a tread with inner timing-belt teeth and outer micropatterns generated from the method of FIG. 6.

The molding process provides a continuous, single material elastic belt with timing-belt teeth on the inside (to grip the pulleys/wheels and transfer power from front to back) and micropatterns on the outside to gain traction on the slippery bowel surfaces. For example, FIG. 8 is a diagram of a tread 800 with inner timing-belt teeth 802 and outer micropatterns 804 generated from the method 600 of FIG. 6. Continuity of the belt reduces traction/adhesion issues on the bowel surface, increases safety within the human body, and reduces wear of a noncontinuous belt that could delaminate or break from fatigue much sooner. The continuous belt allows for larger contact area on the colon mucosa, providing better traction and thus locomotion of the device, while still being a soft material that is safe for the colon tissue. The design of the OM/IM1/IM2 may allow for tunable thickness belts, depending on the application. Flexibility of the molded silicone (with negative micropatterns) allows easy peeling off without damaging delicate pillars, and the flexible mold can be reused. Use of a traditional mold for the negative pillars may separate in half or quarters from the inner mold, damaging pillars. Also, the PDMS material can be changed to any injectable and medically safe elastomer.

Methods of using the colonoscopy/endoscopy procedures of the capsule robotic device 100 may also provide benefits over previous procedures. For example, the device is self-propelled (i.e. moves by locomoting itself with motors, not pushed/pulled from an outside force such as traditional endoscopes or magnets). The treaded design of the device 100 provides more contact area for locomotion/distribution of weight, tunable outer patterns for traction, soft treads increase safety. The angled treads provide for better contact on a nonplanar deformable surface. Further, the robotic device 100 may be "smart-sensing" such that it has numerous sensors on an already miniaturized device, giving it capabilities to understand its environment, learn, map, decide, etc. all autonomously.

The robotic device 100 also provides a tether that allows for various colonoscopy related procedures. For example, the device 100 allows for biopsy/tissue sampling/polypectomy that is common during colonoscopy (i.e., tissue must be removed from the body, multiple times, and each sample individually logged/stored for lab analysis). Insufflation may be performed via an air channel to inflate the colon lumen for device navigation as well as getting a full view of the mucosa and irrigation may be performed via a water jet to clean the colon, remove obstructions/obstacles, and clean camera lens. Related to the insufflation/irrigation, either channel can be used for suction as well, for reducing air pressure in colon or removing excess liquid. Power consumption of the device 100 may be less than traditional colonoscopes as sensors, motors, etc. may be limited in function and power if only using a battery and retrieval of the device is safer than other types of colonoscopes.

Performance requirements & design constraints can also be bundled with full parameterization of gear geometries to create a tool for optimizing the size of the device. Basically, it is a tool/software that given any required performance (traction, rimpull, acceleration, run-out speed, etc.) will detail the gear geometries needed and the final size of the device, minimized for specific applications. The device 100 can be used with any vehicle performance metrics to spec out motors, gears, and minimize the size of a device, which may be useful for medical applications where minimization is crucial to adopting new devices.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A robotic endoscope device comprising:
    a first double worm drive shaft in communication with a first motor, disposed within a housing, comprising a first screw section and a second screw section, wherein a spiraling component of the first screw section is in a different direction than a spiraling component of the second screw section;
    a first worm gear threadably engaged with the first screw section of the first double worm drive shaft and translating rotation of the first screw section of the first double worm drive shaft to rotation of a first continuous track assembly in a first direction; and
    a second worm gear threadably engaged with the second screw section of the first double worm drive shaft and translating rotation of the second screw section of the first double worm drive shaft to rotation of a second continuous track assembly in a second direction simultaneously with the rotation of the first continuous track assembly, the rotation of the second continuous track assembly in a direction different than the rotation of the first continuous track assembly.

2. The robotic endoscope device of claim 1 wherein the first screw section of the first double worm drive shaft comprises a right-handed spiraling and the second screw section of the double worm drive shaft comprises a left-hand spiraling.

3. The robotic endoscope device of claim 1 further comprising an idler gear threadably engaged with the second worm gear and the second continuous track assembly to transmit the rotation of the second screw section to the rotation of the second continuous track assembly.

4. The robotic endoscope device of claim 1 wherein the housing comprises an upper portion and a lower portion, the upper portion of the housing comprising a first angled upper continuous track slot through which the second continuous track assembly extends; and wherein the lower portion of the housing comprises a first angled lower continuous track slot through which the first continuous track assembly extends.

5. The robotic endoscope device of claim 4 further comprising:
    a second double worm drive shaft, disposed within the housing between the upper portion and the lower portion, comprising a first screw section comprising right-handed spiraling and a second screw section comprising left-handed spiraling.

6. The robotic endoscope device of claim 5 further comprising:
    a third worm gear threadably engaged with the first screw section of the second double worm drive shaft and engaged with a third continuous track assembly, the third worm gear transmitting rotation of the second double worm drive shaft to rotation of the third continuous track assembly; and
    a fourth worm gear threadably engaged with the second screw section of the second double worm drive shaft, the fourth worm gear rotating opposite the rotation of the third worm gear in response to rotation of the second double worm drive shaft.

7. The robotic endoscope device of claim 6 wherein the upper portion of the housing further comprises a second angled upper continuous track slot substantially perpendicular to the first angled upper continuous track slot and through which the fourth continuous track assembly extends; and
    wherein the lower portion of the housing comprises a second angled lower continuous track slot substantially perpendicular to the first angled lower continuous track slot through which the third continuous track assembly extends.

8. The robotic endoscope device of claim 5 wherein the first motor is configured to rotate the first double worm drive shaft in response to a first activation signal, the device further comprising:
    a second motor connected to the second double worm drive shaft configured to rotate the second double worm drive shaft, independent of the first double worm drive shaft, in response to a second activation signal.

9. The robotic endoscope device of claim 8 further comprising:
    a tether extending from a back portion of the housing, the tether comprising a tube housing one or more control electrical cables in electrical communication with the first motor and the second motor to activate the first motor and the second motor.

10. A surgical method for a colonoscopy comprising:
    locating a self-propelled endoscope device in a gastrointestinal tract of a subject;
    transmitting a first drive signal to a first motor of the endoscope device to rotate a first double worm drive shaft, wherein rotation of the first double worm drive shaft causes a first continuous track assembly to rotate in a first rotational direction and a second continuous track assembly to simultaneously rotate in a second rotational direction opposite the first rotation direction to propel the endoscope device; and
    transmitting a second drive signal to a second motor of the endoscope device to rotate a second double worm drive shaft independent of the first double worm drive shaft, wherein rotation of the second double worm drive shaft causes a third continuous track assembly to rotate independent of the first continuous track assembly and a fourth continuous track assembly to rotate independent of the second continuous track assembly, the first drive signal and the second drive signal transmitted to propel the endoscope device within the gastro-intestinal tract.

11. The surgical method of claim 10 wherein the rotation of the second double worm drive shaft causes the third continuous track assembly to rotate in the first rotational direction and the fourth continuous track assembly to rotate in the second rotational direction opposite the first direction to propel the endoscope device forward.

12. The surgical method of claim 10 wherein the rotation of the second double worm drive shaft causes the third continuous track assembly to rotate in the second rotational direction and the fourth continuous track assembly to rotate in the first rotational direction to skid-steer the endoscope device.

13. The surgical method of claim 10 wherein the second continuous track assembly is angled with respect to the first continuous track assembly and the fourth continuous track assembly.

14. The surgical method of claim 10 wherein the second continuous track assembly and fourth continuous track assembly both comprise a plurality of cylindrical treads extending perpendicular from a corresponding track surface.

15. The surgical method of claim 10 wherein transmitting the first drive signal and the second drive signal comprises sending an electrical control signal through a tether extending from a back portion of the endoscope device, the tether housing one or more control electrical cables in electrical communication with a first motor and a second motor of the endoscope device.

* * * * *